US009631981B2

(12) United States Patent
Jun et al.

(10) Patent No.: US 9,631,981 B2
(45) Date of Patent: Apr. 25, 2017

(54) APPARATUS AND METHOD FOR MEASURING THERMOELECTRIC DEVICE

(71) Applicant: Electronics and Telecommunications Research Institute, Daejeon (KR)

(72) Inventors: Dong Suk Jun, Daejeon (KR); Moon Gyu Jang, Daejeon (KR); Won Chul Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 434 days.

(21) Appl. No.: 14/330,621

(22) Filed: Jul. 14, 2014

(65) Prior Publication Data

US 2015/0092812 A1    Apr. 2, 2015

(30) Foreign Application Priority Data

Sep. 30, 2013 (KR) .................. 10-2013-0116665
Jan. 21, 2014 (KR) .................. 10-2014-0007315

(51) Int. Cl.
*G01K 17/06* (2006.01)
*H01L 35/00* (2006.01)
*G01K 7/08* (2006.01)
*G01N 25/18* (2006.01)

(52) U.S. Cl.
CPC .............. *G01K 7/08* (2013.01); *G01N 25/18* (2013.01)

(58) Field of Classification Search
CPC ........... G01N 25/18; H01L 35/00; G01K 7/08
See application file for complete search history.

(56) References Cited

U.S. PATENT DOCUMENTS 4,639,883 A * 1/1987 Michaelis ............... F25B 21/02
                                                    374/182
5,940,784 A * 8/1999 El-Husayni .......... G01N 25/005
                                                    374/43
6,402,369 B1 * 6/2002 Ludington ........... G01N 25/482
                                                    136/204

(Continued)

FOREIGN PATENT DOCUMENTS

DE         10200703936 A1 *  2/2009
GB         1245054 A *       9/1971  ............. G01N 25/18

(Continued)

*Primary Examiner* — Gail Kaplan Verbitsky
(74) *Attorney, Agent, or Firm* — Rabin & Berdo, P.C.

(57) ABSTRACT

Provided is an apparatus for measuring a thermoelectric device. The apparatus includes a high temperature heater controlling a temperature of a first side of a sample, a low temperature heater controlling a temperature of a second side of the sample, a fine control heater controlling the temperature of the first side of the sample by a smaller unit than the high temperature heater, a temperature control and voltage measuring unit controlling the high temperature heater, the low temperature heater, and the fine control heater and measuring voltages of the first and second sides of the sample, and a thermal conductivity measuring unit measuring thermal conductivity of the sample by using a high temperature output voltage generated in the first side of the sample and a low temperature output voltage generated in the second side of the sample.

10 Claims, 7 Drawing Sheets

(56) References Cited

U.S. PATENT DOCUMENTS

| | | | | |
|---|---|---|---|---|
| 6,923,570 | B2 * | 8/2005 | Shih | G01N 3/18 |
| | | | | 374/30 |
| 7,226,206 | B2 * | 6/2007 | Romes | G01K 17/08 |
| | | | | 374/135 |
| 8,212,212 | B2 | 7/2012 | Park et al. | |
| 2011/0165333 | A1 * | 7/2011 | Gasworth | C23C 4/134 |
| | | | | 427/446 |
| 2012/0294329 | A1 * | 11/2012 | Miller | G01N 25/18 |
| | | | | 374/44 |

FOREIGN PATENT DOCUMENTS

| | | | |
|---|---|---|---|
| JP | 07306724 A | * | 11/1995 |
| JP | 2013113649 A | * | 6/2013 |
| KR | 10-2011-0130760 A | | 12/2011 |
| KR | 10-2013-0028470 A | | 3/2013 |
| KR | 20150037458 A | * | 4/2015 |

* cited by examiner

APPARATUS AND METHOD FOR MEASURING THERMOELECTRIC DEVICE

CROSS-REFERENCE TO RELATED APPLICATIONS

This U.S. non-provisional patent application claims priority under 35 U.S.C. §119 of Korean Patent Application Nos. 10-2013-0116665, filed on Sep. 30, 2013, and 10-2014-0007315, filed on Jan. 21, 2014, the entire contents of which are hereby incorporated by reference.

FIELD

The present invention disclosed herein relates to a measuring apparatus, and more particularly, to a thermoelectric device measuring apparatus for measuring properties of a thermoelectric device while maintaining a stable temperature.

BACKGROUND

A closed circuit is formed by connecting both ends of two different metal conducting wires to one another and a temperature difference is applied to both ends, thereby generating a potential difference between two contact points. A phenomenon described above is designated as a thermoelectric phenomenon. The potential difference generated herein is designated as a thermoelectric force.

Thermoelectric devices use the thermoelectric phenomenon described above. Thermoelectric devices show Seebeck effect and Peltier effect. Both ends of two kinds of metals or semiconductors join one another and a temperature difference is applied to both ends, thereby generating an electromotive force in a circuit. This is designated as Seebeck effect. Two kinds of metals or semiconductors join one another and a current is applied, thereby absorbing or generating heat at a join. This is designated as Peltier effect.

When a single thermocouple is used to measure properties of a thermoelectric device, although using any one of a direct current and an alternating current, it is difficult to heat a contact point of the thermocouple using Peltier effect simultaneously with measuring a temperature of the contact point of the thermocouple using Seebeck effect.

SUMMARY OF THE INVENTION

The present invention provides an apparatus and a method for measuring properties of a thermoelectric device while applying and maintaining a stable temperature difference.

Embodiments of the present invention provide an apparatus for measuring a thermoelectric device including a high temperature heater controlling a temperature of a first side of a sample, a low temperature heater controlling a temperature of a second side of the sample, a fine control heater controlling the temperature of the first side of the sample by a smaller unit than the high temperature heater, a temperature control and voltage measuring unit controlling the high temperature heater, the low temperature heater, and the fine control heater and measuring voltages of the first and second sides of the sample, and a thermal conductivity measuring unit measuring thermal conductivity of the sample by using a high temperature output voltage generated in the first side of the sample and a low temperature output voltage generated in the second side of the sample.

In some embodiments, the temperature control and voltage measuring unit may include a first temperature controller applying a high temperature input voltage to the high temperature heater to control the temperature of the first side of the sample, a first measurer applying a variation input voltage to control the temperature of the first side of the sample by a smaller unit than the high temperature heater and measuring the high temperature output voltage, a second temperature controller applying a low temperature input voltage to the lower temperature heater to control the temperature of the second side of the sample, and a second measurer measuring the low output voltage.

In other embodiments, the apparatus may include a high temperature plate electrode in contact with the first side of the sample and a first sensor measuring a voltage and a current of the high temperature plate electrode to calculate the temperature of the first side of the sample. Herein, the first temperature controller may control the high temperature input voltage according to the temperature of the first side of the sample and the first measurer may measure the high temperature output voltage through the high temperature plate electrode and controls the variation input voltage according to the high temperature output voltage.

In still other embodiments, the apparatus may include a low temperature plate electrode in contact with the second side of the sample and a second sensor measuring a voltage and a current of the low temperature plate electrode to calculate the temperature of the second side of the sample. Herein, the second temperature controller may control the low temperature input voltage according to the temperature of the second side of the sample, and the second measurer may measure the low temperature output voltage through the low temperature plate electrode.

In even other embodiments, the temperature control and voltage measuring unit may include a third measurer measuring a voltage and a current by a smaller unit than the second temperature controller and the third measurer may calculate the temperature of the second side of the sample according to a voltage and a current of the low temperature plate electrode measured by the second sensor.

In yet other embodiments, the first measurer may control the fine control heater to vary only with a unit temperature and measure the high temperature output voltage according to a variation of the unit temperature.

In further embodiments, the thermal conductivity measuring unit may include a frequency generator generating a reference voltage, a thermoelectric voltage amplification part generating a lock-in voltage using the high and low temperature output voltages, and a lock-in amplifier measuring the thermal conductivity of the sample using the reference voltage and the lock-in voltage.

In still further embodiments, the thermoelectric voltage amplification part may include a potentiometer connected to the sample in series and controlling resistance to remove a noise signal from the high and low temperature voltages and a comparator comparing an output voltage of the potentiometer with the high and low temperature output voltages and outputting the lock-in voltage.

In even further embodiments, the thermoelectric voltage amplification part may further include a first amplifier amplifying the output voltage of the potentiometer and transmitting the amplified output voltage to the comparator and a second amplifier amplifying a voltage difference between the high and low temperature output voltages and transmitting the amplified voltage difference to the comparator.

In yet further embodiments, the lock-in amplifier may change the lock-in voltage according to the reference voltage and may output a thermoelectric voltage corresponding to a preset frequency.

In much further embodiments, the first side of the sample may be opposite to the second side of the sample.

In other embodiments of the present invention, a method of measuring a thermoelectric device, include heating a sample by applying a reference voltage, measuring a high temperature output voltage of a first side of the heated sample, measuring a low temperature output voltage of a second side of the heated sample, the second side being opposite to the first side of the heated sample, and determining a thermoelectric voltage having a preset frequency according to a difference between the high and low temperature output voltages based on the reference voltage.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
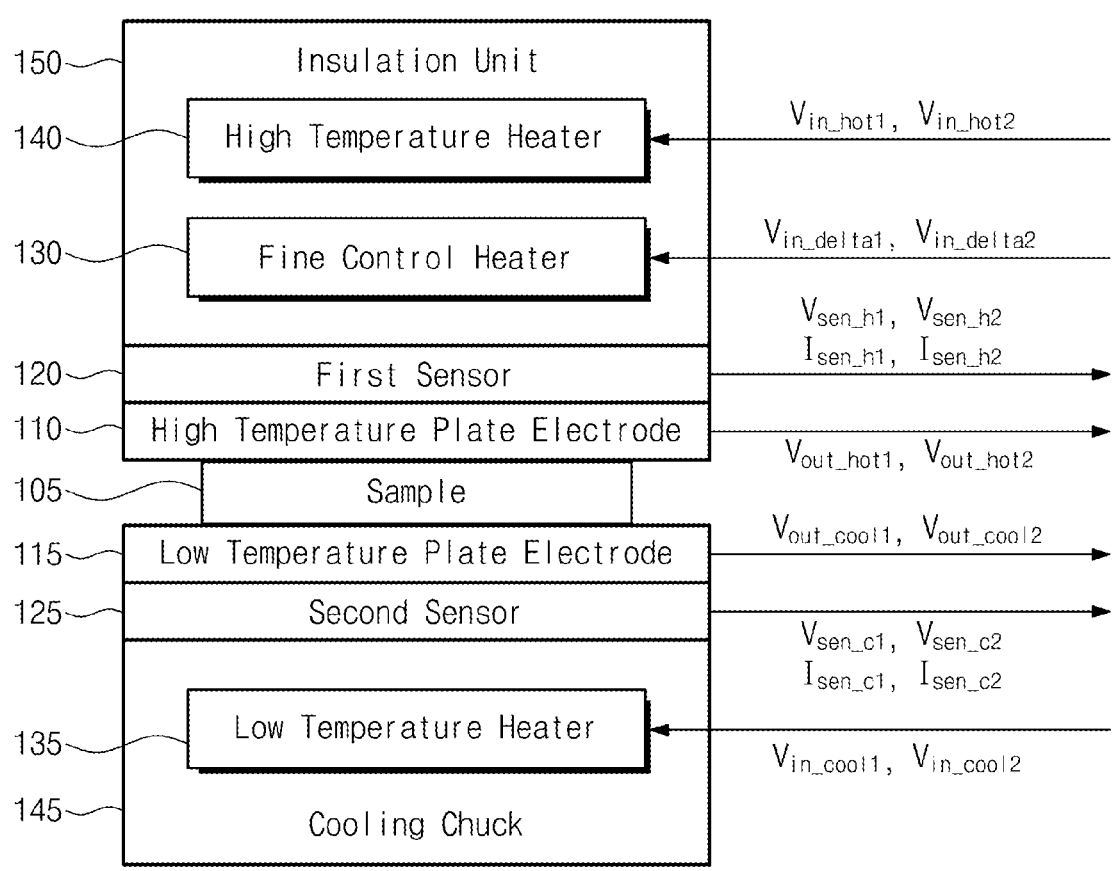
FIG. 1 is a view of a thermoelectric device measuring jig according to an embodiment of the present invention.

It will be understood that both a general description in the above and a following description are exemplary and an additional description for embodiments is provided. Reference numerals are mentioned in detail in exemplary embodiments and examples thereof are shown in the attached drawings. In any possible case, identical reference numerals are used for referring to identical or similar elements in the description and drawings.

Hereinafter, a thermoelectric device measuring apparatus is used as an electric device to describe features and functions of embodiments. However, a person of ordinary skill in the art may easily understand other advantages and performances of the embodiments with reference to a disclosure hereafter. Also, the inventive concept will be provided or applied through other embodiments. In addition, the embodiments may be modified or vary according to points of view and applications without considerably deviating from the range, technical thoughts and others of the inventive concept.

FIG. 1 is a view of a thermoelectric device measuring jig 100 according to an embodiment of the present invention. Referring to FIG. 1, the thermoelectric device measuring jig 100 may fix a sample 105 to be between a high temperature plate electrode 110 and a low temperature plate electrode 115 and may heat the sample 105. For example, the sample 105 may be a small piece of a thermoelectric device.

A first side of the sample 105 may be in contact with the high temperature plate electrode 110. A high temperature heater 140 or a fine control heater 130 may control a temperature of the first side of the sample 105. The high temperature heater 140 may be connected to high temperature input voltage terminals $V_{in\_hot1}$ and $V_{in\_hot2}$. The high temperature heater 140 may receive voltages from the high temperature input voltage terminals $V_{in\_hot1}$ and $V_{in\_hot2}$ and may increase a temperature. The fine control heater 130 may be connected to variation input voltage terminals $V_{in\_delta1}$ and $V_{in\_delta2}$. The fine control heater 130 may receive voltages from the variation input terminals $V_{in\_delta1}$ and $V_{in\_delta2}$ and may increase a temperature. For example, the high temperature heater 140 may increase the temperature by 100° C. unit according to the received voltage. The fine control heater 130 may increase the temperature by 1° C. unit according to the received voltage.

An insulation unit 150 may insulate a space including the high temperature heater 140 and the fine control heater 130 from the outside. The insulation unit 150 may allow heat from the high temperature 140 or the fine control heater 130 to be transferred to the high temperature plate electrode 110 without loss. A first sensor 120, in order to measure the temperature of the first side of the sample 105, may be connected to first sensor voltage terminals $V_{sen\_h1}$ and $V_{sen\_h2}$ and first sensor current terminals $I_{sen\_h1}$ and $I_{sen\_h2}$. For example, the first sensor 120 may measure a voltage and a current of the first side of the sample 105. The temperature of the first side of the sample 105 may be calculated using the voltage and current of the first side of the sample 105. The high temperature plate electrode 110 may be connected to high temperature output voltage terminals $V_{out\_hot1}$ and $V_{out\_hot2}$. The high temperature plate electrode 110 may measure the voltage of the first side of the sample 105 according to a temperature.

A second side of the sample 105 may be in contact with the low temperature plate electrode 115. The second side of the sample 105 may be located opposite to the first side of the sample 105. A low temperature heater 135 may control a temperature of the second side of the sample 105. The low temperature heater 135 may be connected to low temperature input voltage terminals $V_{in\_cool1}$ and $V_{in\_cool2}$. The low temperature heater 135 may increase or decrease a temperature according to voltages received from the low temperature input voltage terminals $V_{in\_cool1}$ and $V_{in\_cool2}$. For example, the low temperature heater 135 may maintain the temperature of the second side of the sample 105 as 0° C. That is, the low temperature heater 135 may control the temperature of the second side of the sample 105 to be lower than the temperature of the first side of the sample 105.

A cooling chuck 145 may insulate the low temperature heater 135 from the outside. The cooling chuck 145 may allow heat of the low temperature heater 135 to be transferred to the second side of the sample 105 without loss. A second sensor 125, in order to measure the temperature of the second side of the sample 105, may be connected to second sensor voltage terminals $V_{sen\_c1}$ and $V_{sen\_c2}$ and second sensor current terminals $I_{sen\_c1}$ and $I_{sen\_c2}$. For example, the second sensor 125 may measure a voltage and a current of the second side of the sample 105. The temperature of the second side of the sample 105 may be calculated using the voltage and current of the second side of the sample 105. The low temperature plate electrode 115 may be connected to low temperature output voltage terminals $V_{out\_cool1}$ and $V_{out\_cool2}$. The low temperature plate electrode 115 may measure the voltage of the second side of the sample 105 according to a temperature.

As described above, the thermoelectric device measuring jig 100 may control the temperature of the sample 105. The thermoelectric device measuring jig 100 includes the fine control heater 130 and may control a temperature by smaller unit than the high temperature heater 140.

Figure 2:
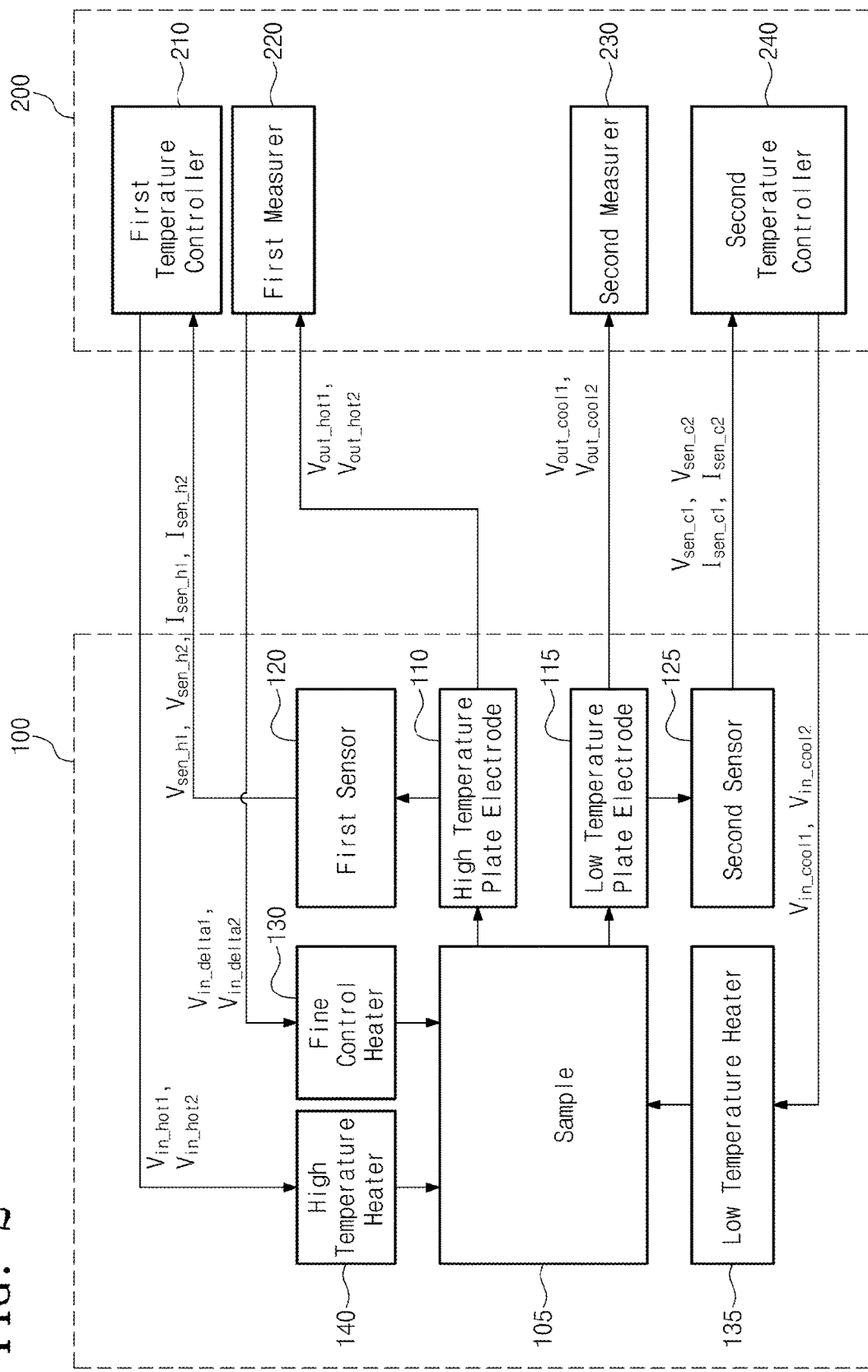
FIG. 2 is a block diagram of a temperature control and Seebeck coefficient measurement system according to an embodiment of the present invention.

FIG. 2 is a block diagram of a temperature control and Seebeck coefficient measurement system according to an embodiment of the present invention. Referring to FIG. 2, there is illustrated a block diagram of the thermoelectric device measuring jig 100. The temperature control measurement system may include the thermoelectric device measuring jig 100 and a temperature control and voltage measuring unit 200.

A first temperature controller 210 may supply a voltage to the high temperature heater 140 through the high temperature input voltage terminals $V_{in\_hot1}$ and $V_{in\_hot2}$. The high temperature heater 140 may control a temperature of the first side of the sample 105 according to the supplied voltage. For example, the high temperature heater 140 may control the temperature of the first side of the sample 105 by 100° C.

Also, the first temperature controller 210 may be connected to the first sensor 120 through the first sensor voltage terminals $V_{sen\_h1}$ and $V_{sen\_h2}$ and the first sensor current terminals $I_{sen\_h1}$ and $I_{sen\_h2}$. The first temperature controller 210 may calculate the temperature of the first side of the sample 105 by using a voltage and a current received from the first sensor 120. For example, the first sensor 120 may measure the voltage and the current of the first side of the sample 105. The temperature of the first side of the sample 105 may be calculated using the voltage and current of the first side of the sample 105. The first temperature controller 210 may control the high temperature heater 140 according to the calculated temperature of the first side of the sample 105.

A first measurer 220 may supply a voltage to the fine control heater 130 through the variation input voltage terminals $V_{in\_delta1}$ and $V_{in\_delta2}$. The fine control heater 130 may control the temperature of the first side of the sample 105 according to the supplied voltage. The fine control heater 130 may control the temperature of the first side of the sample 105 by a smaller unit than the high temperature heater 140. For example, the fine control heater 130 may control the temperature of the first side of the sample 105 by 1° C. unit according to the supplied voltage.

Also, the first measurer 220 may be connected to the high temperature plate electrode 110 through the high temperature output voltage terminals $V_{out\_hot1}$ and $V_{out\_hot2}$. The first measurer 220 may measure the voltage of the first side of the sample 105 through the high temperature plate electrode 110. For example, the first measurer 220 may measure the voltage of the first side of the sample 105 according to the temperature of the first side of the sample 105, which varies by 1° C. unit.

The high temperature plate electrode 110 may be located being in contact with the first side of the sample 105. Accordingly, the high temperature plate electrode 110 may have the same voltage and current as the first side of the sample 105.

A second temperature controller 240 may supply a voltage to the low temperature heater 135 through the low temperature input voltage terminals $V_{in\_cool1}$ and $V_{in\_cool2}$. The low temperature heater 135 may control the temperature of the second side of the sample 105 according to the supplied voltage. The low temperature heater 135 may control the temperature of the second side of the sample 105 to be lower than the high temperature heater 140. For example, the low temperature heater 135 may maintain the temperature of the second side of the sample 105 as 0° C.

Also, the second temperature controller 240 may be connected to the second sensor 125 through the second sensor voltage terminals $V_{sen\_c1}$ and $V_{sen\_c2}$ and the second sensor current terminals $I_{sen\_c1}$ and $I_{sen\_c2}$. The second temperature controller 240 may calculate the temperature of the second side of the sample 105 by using a voltage and a current received from the second sensor 125. For example, the second sensor 125 may measure a voltage and a current of the second side of the sample 105. The temperature of the second side of the sample 105 may be calculated using the voltage and current of the second side of the sample 105. The second temperature controller 240 may control the low temperature heater 135 according to the calculated temperature of the second side of the sample 105.

A second measurer 230 may be connected to the low temperature plate electrode 115 through the low temperature output voltage terminals $V_{out\_cool1}$ and $V_{out\_cool2}$. The second measurer 230 may measure the voltage of the second side of the sample 105 through the low temperature plate electrode 115. For example, the second measurer 230 may measure the voltage of the second side of the sample 105 as the temperature of the first side of the sample 105 varies by 1° C. unit.

The low temperature plate electrode 115 may be located being in contact with the second side of the sample 105. Accordingly, the low temperature plate electrode 115 may have the same voltage and current as the second side of the sample 105.

Elements 210, 220, 230, and 240 in the temperature control and voltage measuring unit 200 may share information with one another.

As described above, the temperature control and Seebeck coefficient measurement system may control the temperatures of the first and second sides of the sample 105. The temperature control and Seebeck coefficient measurement system may measure the voltages and the currents of the first and second sides of the sample 105 according to temperature change. The temperature control and Seebeck coefficient measurement system may control the temperature of the first side of the sample 105 by a smaller unit than the high temperature heater 140 by using the fine control heater 130. For example, the temperature control and Seebeck coefficient measurement system may control the temperature of the first side of the sample 105 by 1° C. unit by using the fine control heater 130. When the temperature of the first side of the sample 105 varies by 1° C. unit, the first and second measurer 220 and 230 may measure the voltages of the first and second sides of the sample 105. The temperature control and Seebeck coefficient measurement system may calculate Seebeck coefficient by using the measured voltages of the first and second sides. Herein, Seebeck coefficient may be defined to be an electromotive force generated by a temperature difference of 1° C.

Figure 3:
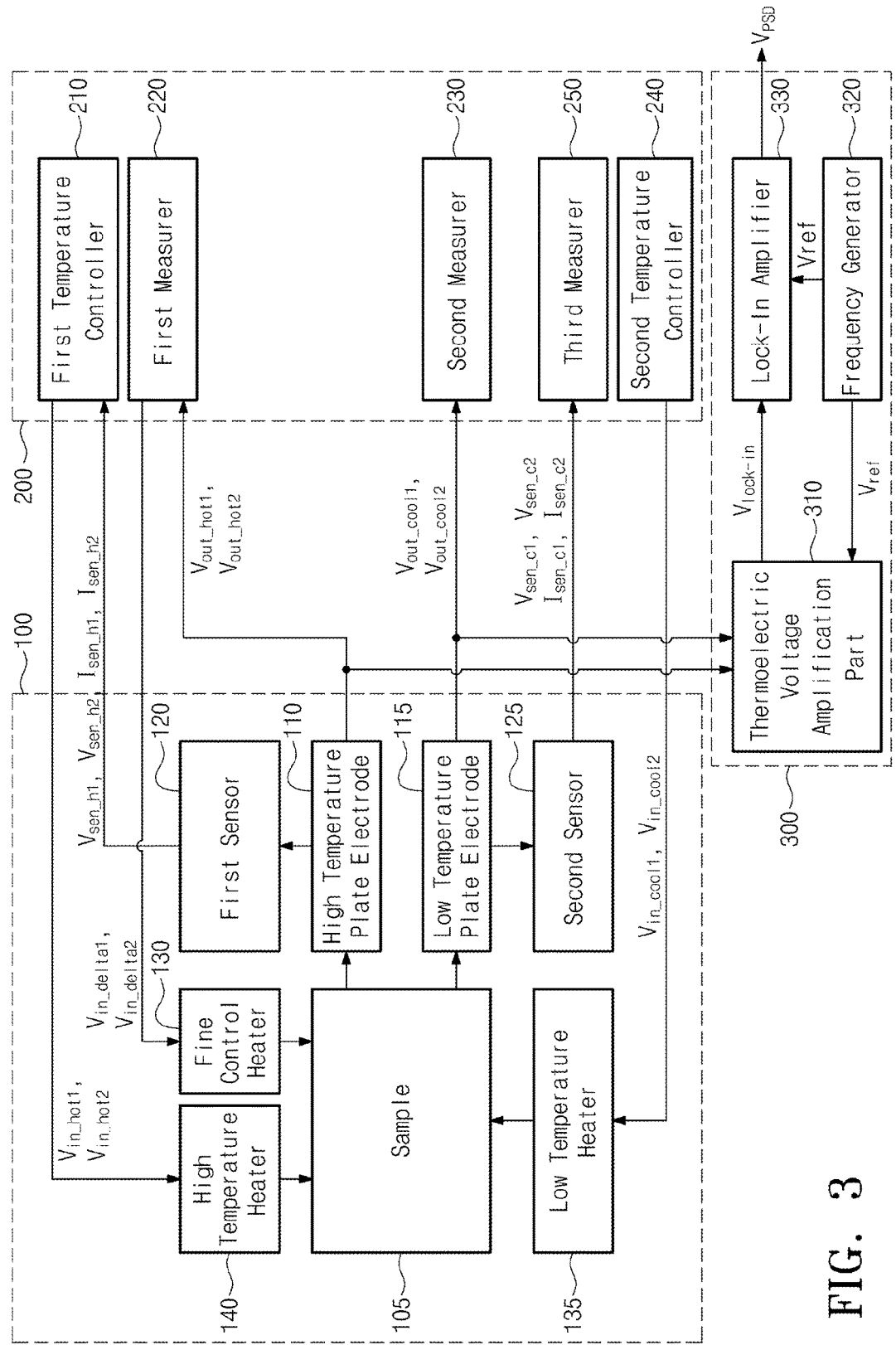
FIG. 3 is a block diagram of a thermal conductivity measurement system for measuring thermal conductivity of a thermoelectric device according to an embodiment of the present invention.

FIG. 3 is a block diagram of a thermal conductivity measurement system for measuring thermal conductivity of a thermoelectric device according to an embodiment of the present invention. The thermal conductivity measurement system may include the thermoelectric device measuring jig 100, the temperature control and voltage measuring unit 200, and a thermal conductivity measuring unit 300.

The first temperature controller 210 may supply a voltage to the high temperature heater 140 through the high temperature input voltage terminals $V_{in\_hot1}$ and $V_{in\_hot2}$. The high temperature heater 140 may control the temperature of the first side of the sample 105 according to the supplied voltage. For example, the high temperature heater 140 may control the temperature of the first side of the sample 105 by 100° C. unit.

Also, the first temperature controller 210 may be connected to the first sensor 120 through the first sensor voltage terminals $V_{sen\_h1}$ and $V_{sen\_h2}$ and the first sensor current terminals $I_{sen\_h1}$ and $I_{sen\_h2}$. The first temperature controller 210 may calculate the temperature of the first side of the sample 105 by using a voltage and a current received from the first sensor 120. For example, the first sensor 120 may measure a voltage and a current of the first side of the sample 105. The temperature of the first side of the sample 105 may be calculated using the voltage and current of the first side of the sample 105. The first temperature controller 210 may control the high temperature heater 140 according to the calculated temperature of the first side of the sample 105.

The first measurer 220 may supply a voltage to the fine control heater 130 through the variation input voltage terminals $V_{in\_delta1}$ and $V_{in\_delta2}$. The fine control heater 130 may control the temperature of the first side of the sample 105 according to the supplied voltage. The fine control heater 130 may control the temperature of the first side of the sample 105 by a smaller unit than the high temperature heater 140. For example, the fine control heater 130 may control the temperature of the first side of the sample 105 by 1° C. according to the supplied voltage.

Also, the first measurer 220 may be connected to the high temperature plate electrode 110 through the high temperature output voltage terminals $V_{out\_hot1}$ and $V_{out\_hot2}$. The first measurer 220 may measure the voltage of the first side of the sample 105 through the high temperature plate electrode 110. For example, the first measurer 220 may measure the voltage of the first side of the sample 105 according to the temperature of the first side of the sample 105, which varies by 1° C. unit.

The high temperature plate electrode 110 may be located being in contact with the first side of the sample 105. Accordingly, the high temperature plate electrode 110 may have the same voltage and current as the first side of the sample 105.

The second temperature controller 240 may supply a voltage to the low temperature heater 135 through the low temperature input voltage terminals $V_{in\_cool1}$ and $V_{in\_cool2}$. The low temperature heater 135 may control the temperature of the second side of the sample 105 according to the supplied voltage. The low temperature heater 135 may control the temperature of the second side of the sample 105 to be lower than the high temperature heater 140. For example, the low temperature heater 135 may maintain the temperature of the second side of the sample 105 as 0° C.

The second measurer 230 may be connected to the low temperature plate electrode 115 through the low temperature output voltage terminals $V_{out\_cool1}$ and $V_{out\_cool2}$. The second measurer 230 may measure the voltage of the second side of the sample 105 through the low temperature plate electrode 115. For example, the second measurer 230 may measure the voltage of the second side of the sample 105 as the temperature of the second side of the sample 105 varies by 1° C. unit.

The low temperature plate electrode 115 may be located being in contact with the second side of the sample 105. Accordingly, the low temperature plate electrode 115 may have the same voltage and current as the second side of the sample 105.

A third measurer 250 may be connected to the second sensor 125 through the second sensor voltage terminals $V_{sen\_c1}$ and $V_{sen\_c2}$ and the second sensor current terminals $I_{sen\_c1}$ and $I_{sen\_c2}$. The third measurer 250 may calculate the temperature of the second side of the sample 105 by using a voltage and a current received from the second sensor 125. For example, the second sensor 125 may measure a voltage and a current of the second side of the sample 105. The temperature of the second side of the sample 105 may be calculated using the voltage and current of the second side of the sample 105. The third measurer 250 may share calculated temperature information of the second side of the sample 105 with the second temperature controller 240. The second temperature controller 240 may control the low temperature heater 135 according to the calculated temperature of the second side of the sample 105. Also, the third measurer 250, for example, may be nano meters. Accordingly, the third measurer 250 may more precisely measure than the first and second measurer 220 and 230.

Elements 210, 220, 230, 240, and 250 in the temperature control and voltage measuring unit 200 may share information with one another.

The thermal conductivity measuring unit 300 may include a thermoelectric voltage amplification part 310, a frequency generator 320, and a lock-in amplifier 330. The frequency generator 320 may transmit a preset reference voltage $V_{ref}$ to the thermoelectric voltage amplification part 310 and the lock-in amplifier 330. The thermoelectric voltage amplification part 310 may be connected to the high temperature voltage terminals $V_{out\_hot1}$ and $V_{out\_hot2}$ and the low temperature output voltage terminals $V_{out\_cool1}$ and $V_{out\_cool2}$. The thermoelectric voltage amplification part 310 may measure a thermoelectric voltage between the first and second sides of the sample 105 through the high temperature voltage terminals $V_{out\_hot1}$ and $V_{out\_hot2}$ and the low temperature output voltage terminals $V_{out\_cool1}$ and $V_{out\_cool2}$. The thermoelectric voltage amplification part 310 may transmit a lock-in voltage $V_{lock-in}$ obtained by removing an alternating current supplied to heat the sample 105 from the thermoelectric voltage between the first and second sides of the sample 105 by using the reference voltage $V_{ref}$ to the lock-in amplifier 330. The lock-in amplifier 330 may output a phase voltage $V_{PSD}$ by using the reference voltage $V_{ref}$ and the lock-in voltage $V_{lock-in}$.

Figure 4:
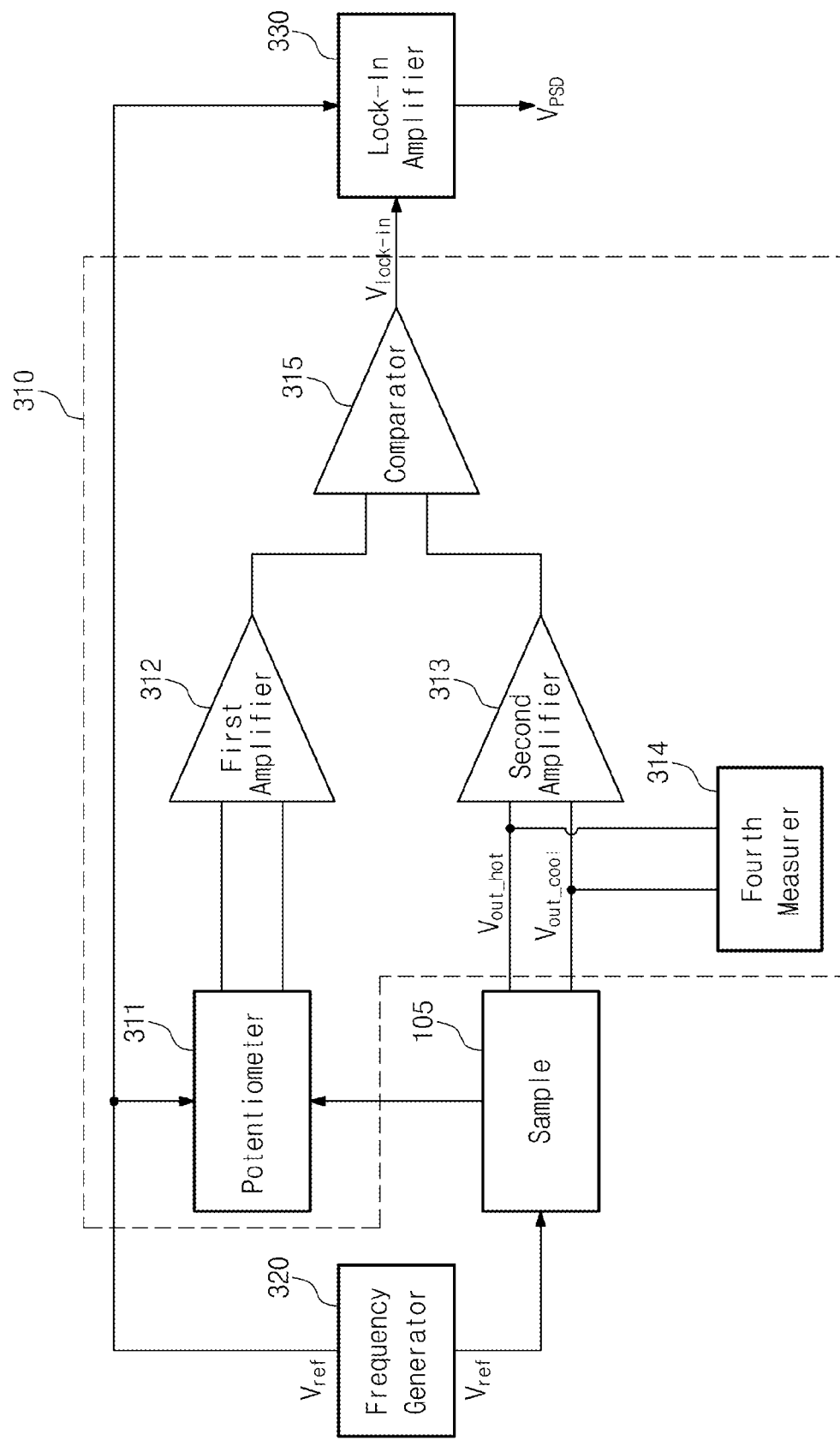
FIG. 4 is a block diagram illustrating a thermoelectric voltage amplifier of FIG. 3 in detail.

FIG. 4 is a block diagram illustrating the thermoelectric voltage amplification part 310 of FIG. 3 in detail. Referring to FIG. 4, the thermoelectric voltage amplification part 310 may include a potentiometer 311, first and second amplifiers 312 and 313, a fourth measurer 314, and a comparator 315.

The frequency generator 320 may apply the reference voltage $V_{ref}$ to the potentiometer 311, the lock-in amplifier 330, and the second side of the sample 105. The first side of the sample 105 may be connected to a variable resistor of the potentiometer 311. Output terminals of the potentiometer 311 may be connected to input terminals of the first amplifiers 312. The first and second sides of the sample 105 may be connected to input terminals of the second amplifier 313. The fourth measurer 314 may be connected to the first and second sides of the sample 105 and may measure a thermoelectric voltage of the sample 105. The comparator 312 may receive output voltages of the first and second amplifiers 312 and 313 and may transmit the lock-in voltage $V_{lock-in}$ to the lock-in amplifier 330. The lock-in amplifier 330 may output the phase voltage $V_{PSD}$ by using the reference voltage $V_{ref}$ and the lock-in voltage $V_{lock-in}$.

The lock-in amplifier 330 may separate the thermoelectric voltage generated in the sample 105 from contact points among the high and low temperature plate electrodes 110 and 115 and the sample 105. The lock-in amplifier 330 may select a voltage signal having a certain frequency from voltage signals having various frequencies generated in the sample 105. The lock-in amplifier 330 may supply the alternating current for heating the high and low temperature plate electrodes 110 and 115.

The potentiometer 311 may include the variable resistor. The variable resistor of the potentiometer 311 may be connected to the high and low temperature plate electrodes 110 and 115 in series.

The variable resistor of the potentiometer 311 may remove a voltage signal having a frequency of 1 ω supplied to heat the high and low temperature plate electrodes 110 and 115. Accordingly, measurement sensitivity may be improved. The variable resistor of the potentiometer 311 may be used to remove a noise signal included in supplied power. The variable resistor of the potentiometer 311 may prevent a change in resistance caused by a temperature difference of the high and low temperature plate electrodes 110 and 115 from having an effect on a current flowing through a circuit of the thermoelectric voltage amplification part 310. Accordingly, the variable resistor of the potentiometer 311 may uniformly maintain a level of the current flowing through the circuit of the thermoelectric voltage amplification part 310 while a thermoelectric voltage is being measured. For example, the variable resistor of the potentiometer 311 may be set to be much greater than a resistor of the sample 105.

The second amplifier 313 may amplify thermoelectric voltages generated in the high and low temperature plate electrodes 110 and 115.

The level of the variable resistor of the potentiometer 311 is controlled to be identical to those of resistors of the high and low temperature plate electrodes 110 and 115, the same voltage is allowed to be applied to the variable resistor of the potentiometer 311 and the high and low temperature plate electrodes 110 and 115. The lock-in amplifier 330 may exclude the voltages applied through the variable resistor of the potentiometer 311 and the high and low temperature plate electrodes 110 and 115. Accordingly, the lock-in amplifier 330 may measure voltage signals having frequencies of 2 ω and 3 ω generated in the high and low temperature plate electrodes 110 and 115. The lock-in amplifier 330 may measure thermal conductivity of the sample 105 by using the voltage signals having frequencies of 2 ω and 3 ω.

Herein, the reference voltage $V_{ref}$ generated by the frequency generator 320 is obtained by using Equation 1 as follows.

$$V_{ref} = V_{sig} \sin(\omega_r t + \theta_{sig}) \quad \text{Equation (1)}$$

The lock-in voltage $V_{lock-in}$ transmitted to the lock-in amplifier 330 by the thermoelectric voltage amplification part 310 is obtained by using Equation 2 as follows.

$$V_{lock-in} = V_L \sin(\omega_L t + \theta_{ref}) \quad \text{Equation (2)}$$

The phase voltage $V_{PSD}$ of the reference voltage $V_{ref}$ and the lock-in voltage $V_{lock-in}$ is obtained by using Equation 3 as follows.

$$V_{PSD} = V_{sig} V_L \sin(\omega_r t + \theta_{sig}) \sin(\omega_L t + \theta_{ref}) = \tfrac{1}{2} V_{sig} V_L [\cos([\omega_r - \omega_L] t + \theta_{sig} - \theta_{ref}) + \cos([\omega_r + \omega_L] t + \theta_{sig} + \theta_{ref})] \quad \text{Equation (3)}$$

In a condition of ωr=ωL, a direct current output component of the phase voltage $V_{PSD}$ is obtained by using Equation 4 as follows.

$$V_{PSD} = \tfrac{1}{2} V_{sig} V_L \cos(\theta_{sig} - \theta_{ref}) \quad \text{Equation (4)}$$

Also, the lock-in amplifier 330 may remove a noise component by using a low frequency filter. The lock-in amplifier 330 may have parameters as shown in Equations 5 to 8. The parameters may include inphase X, antiphase Y, amplitude R, phase θ.

$$X = V_{sig} \cos\theta \quad \text{Equation (5)}$$

$$Y = V_{sig} \sin\theta \quad \text{Equation (6)}$$

$$R = \sqrt{X^2 + Y^2} = V_{sig} \quad \text{Equation (7)}$$

$$\theta = \tan^{-1}\left(\frac{Y}{X}\right) \quad \text{Equation (8)}$$

An alternating current $I_{h,o}(t)$ flowing through the high temperature heater 140 or the fine control heater 130 may be obtained by using Equation 9 as follows.

$$I_{h,o}(t) = I_{h,o} \cos(\omega t) \quad \text{Equation (9)}$$

Herein, Joule heating may be generated by the alternating current $I_{h,o}(t)$. A relation with respect to Joule heating is the same as Equation 10 as follows.

$$P_h(t) = I_{h,o}^2 R_{h,o} \cos^2(\omega t) = \tfrac{1}{2} I_{h,o}^2 R_{h,o} + \cos(2\omega t)) \quad \text{Equation (10)}$$

Herein, power $R_h(t)$ is heater power. Resistance $R_{h,o}$ is heater resistance.

A current Iho.0 is a heater current of a peak of amplitude with a frequency of ω. The heater power $R_h(t)$ includes a direct current component $P_{DC}$ and an alternating current component $P_{AC}$. The direct current component $P_{DC}$ and the alternating current component $P_{AC}$ of the heater power $R_h(t)$ are the same as Equations 11 and 12 as follows, respectively.

$$P_{DC} = \tfrac{1}{2} I_{h,o}^2 R_{h,o} = \tfrac{1}{2} P_{h,o} \quad \text{Equation (11)}$$

$$P_{AC} = \tfrac{1}{2} I_{h,o}^2 R_{h,o} \cos(2\omega t) \quad \text{Equation (12)}$$

Average power $P_{rms}$ is the same as Equation 13 as follows. Also, the average power $P_{rms}$ is identical to the direct current component $P_{DC}$ of the heater power $R_h(t)$.

$$P_{rms} = I_{h,rms}^2 R_{h,o} = P_{DC} \quad \text{Equation (13)}$$

Herein, a heater average current $I_{h,rms}$ is the same as Equation 14 as follows.

$$I_{h,rms} = \sqrt{\frac{1}{\tau} \int_0^\tau I_{h,o}^2(t)\,dt} = I_{h,o}\sqrt{\frac{\omega}{2\pi} \int_0^{\frac{2\pi}{\omega}} \cos^2(\omega t)\,dt} = \frac{I_{h,o}}{\sqrt{2}} \quad \text{Equation (14)}$$

Also, when temperatures of the fine control heater 130 and the high temperature heater 140 and the high and low temperature plate electrodes 110 and 150 vary, the heater power $R_h(t)$ may be generated. A component of the heater power $R_h(t)$ may be expressed as a temperature different ΔT. The temperature difference ΔT may include a direct current component $\Delta T_{DC}$ and an alternating current component $\Delta T_{AC}$. The temperature difference ΔT is the same as Equation 15 as follows.

$$\Delta T = \Delta T_{DC} + |\Delta T_{AC}|\cos(2\omega t + \phi) \quad \text{Equation (15)}$$

Herein, heater resistance $R_h(t)$ has a relation as Equation 16 as follows.

$$R_h(t)=R_{h,o}(1+\beta_h\Delta T_{DC})+\beta_h|\Delta T_{AC}|\cos(2\omega t+\phi)$$ Equation (16)

Herein, a voltage $V_h(t)$ between the first and second sides of the sample 105 is the same as Equation 17 as follows.

$$V_h(t)=I_{h,o}R_{h,o}[(1+\beta_h\Delta T_{DC})\cos(\omega t)+\tfrac{1}{2}\beta_h\Delta T_{AC}|\cos(\omega t+\phi)+\tfrac{1}{2}\beta_h|\Delta T_{AC}|\cos(3\omega t+\phi)]$$ Equation (17)

A harmony voltage of the sample 105 includes thermal conductivity. The thermal conductivity $V_{h,3\omega}(t)$ is a function of phase and temperature. The thermal conductivity $V_{h,3\omega}(t)$ is the same as Equations 18 and 19 as follows.

$$V_{h,3\omega}(t)=\tfrac{1}{2}V_{h,o}\beta_h\Delta T_{AC}$$ Equation (18)

$$V_{h,3\omega}=V_{h,3\omega,x}+iV_{h,3\omega,y}$$ Equation (19)

Also, the alternating current component $\Delta T_{AC}$ is the same as Equation 20 as follows.

$$\Delta T_{AC}=\Delta T_{AC,x}+i\Delta T_{AC,y}$$ Equation (20)

In the above, the thermal conductivity measuring unit 300 may measure a voltage signal having a frequency of 3 ω according to a change in temperature of the sample 105. Accordingly, the thermal conductivity measurement system may measure the thermal conductivity of the sample 105 while applying heat to the high and low temperature plate electrode using an alternating current.

Figure 5:
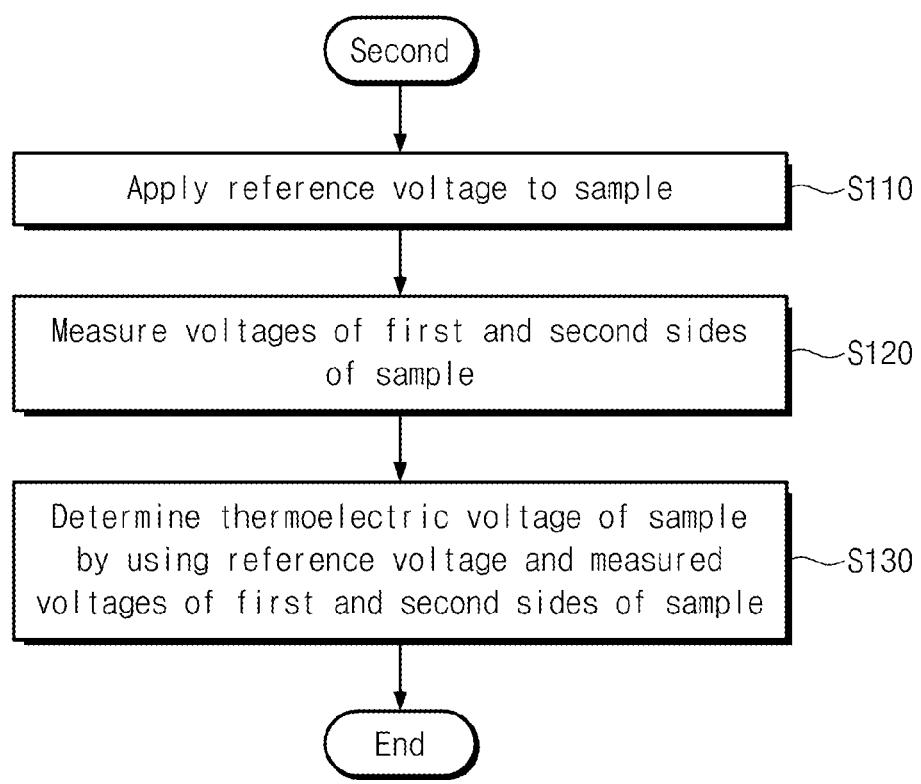
FIG. 5 is a flowchart illustrating a thermoelectric device measuring method according to an embodiment of the present invention.

FIG. 5 is a flowchart illustrating a thermoelectric device measuring method according to an embodiment of the present invention. Referring to FIG. 5, the thermal conductivity measurement system of FIG. 3 may measure the thermal conductivity of the sample 105.

In S110, the frequency generator 320 may apply a reference voltage $V_{ref}$ to the sample 105. A temperature of the sample 105 may be increased by the applied reference voltage $V_{ref}$.

In S120, voltages of the first and second sides of the sample 105 may be measured by the high and low temperature plate electrodes 110 and 115. The measured voltages of the first and second sides of the sample 105 may be transmitted to the thermoelectric voltage amplification part 310. The thermoelectric voltage amplification part 310 may generate a lock-in voltage $V_{lock-in}$ by using the reference voltage $V_{ref}$ and the measured voltages of the first and second sides of the sample 105 and may transmit the lock-in voltage $V_{lock-in}$ to the lock-in amplifier 330.

In S130, the lock-in amplifier 330 may determine a thermoelectric voltage corresponding to a preset frequency by using the lock-in voltage $V_{lock-in}$ and the reference voltage $V_{ref}$.

Thermal conductivity of the sample 105 may be measured through operations S110 to S130 referring to the equations described with reference to FIG. 4.

Figure 6:
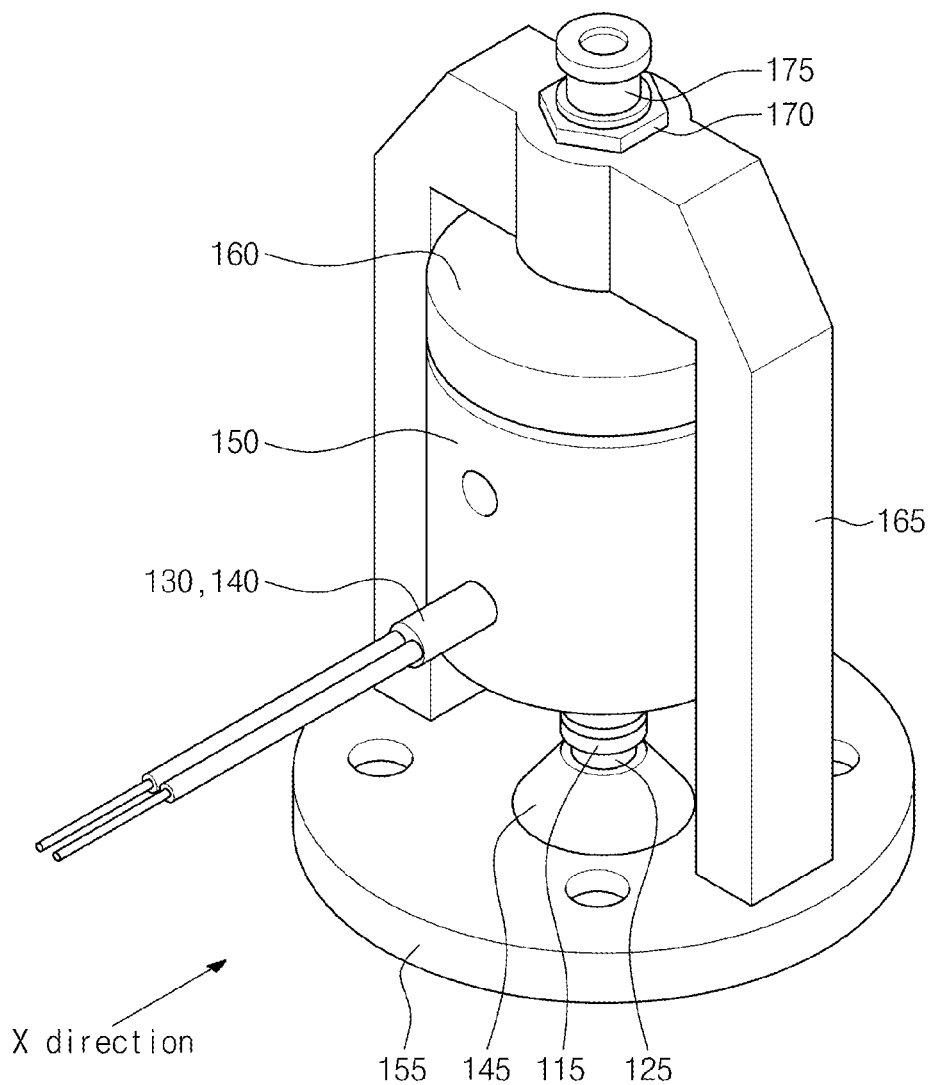
FIG. 6 is a perspective view of the thermoelectric device measuring jig of FIG. 1.

FIG. 6 is a perspective view of the thermoelectric device measuring jig 100. Referring to FIG. 6, the thermoelectric device measuring jig 100 may be fixed using a supporting plate 155 and a center supporting frame 165. While manufacturing the thermoelectric device measuring jig 100, the supporting plate 155 and the center supporting frame 165 may be manufactured to prevent thermal loss. A bottom surface of the cooling chuck 145 may be electrically insulated. The cooling chuck 145 may be manufactured to have high thermal conductivity.

The cooling chuck 145 may be located in a center of the supporting plate 155. The insulation unit 150 may be located in the center supporting frame 165. The first and second sensors 120 and 125, the high and low temperature plate electrodes 110 and 115, and the sample 105 may be located between the insulation unit 150 and the cooling chuck 145. The first sensor 120 and the high temperature plate electrode 110 may be fixed being in contact with the insulation unit 150. The second sensor 125 and the low temperature plate electrode 115 may be fixed being in contact with the cooling chuck 145. The high temperature heater 140 and the fine control heater 130 may be installed in the insulation unit 150. Connecting cables of the high temperature heater 140 and the fine control heater 130 may be connected to a side of the insulation unit 150.

A fixing nut 170 of an air cylinder and a body 175 of the air cylinder may uniformly maintain pressure applied to the sample 105 and the high and low temperature plate electrodes 110 and 115. A pressure sensor 160 may measure the pressure applied to the sample 105. The pressure sensor 160 may uniformly maintain the pressure applied to the sample 105.

Figure 7:
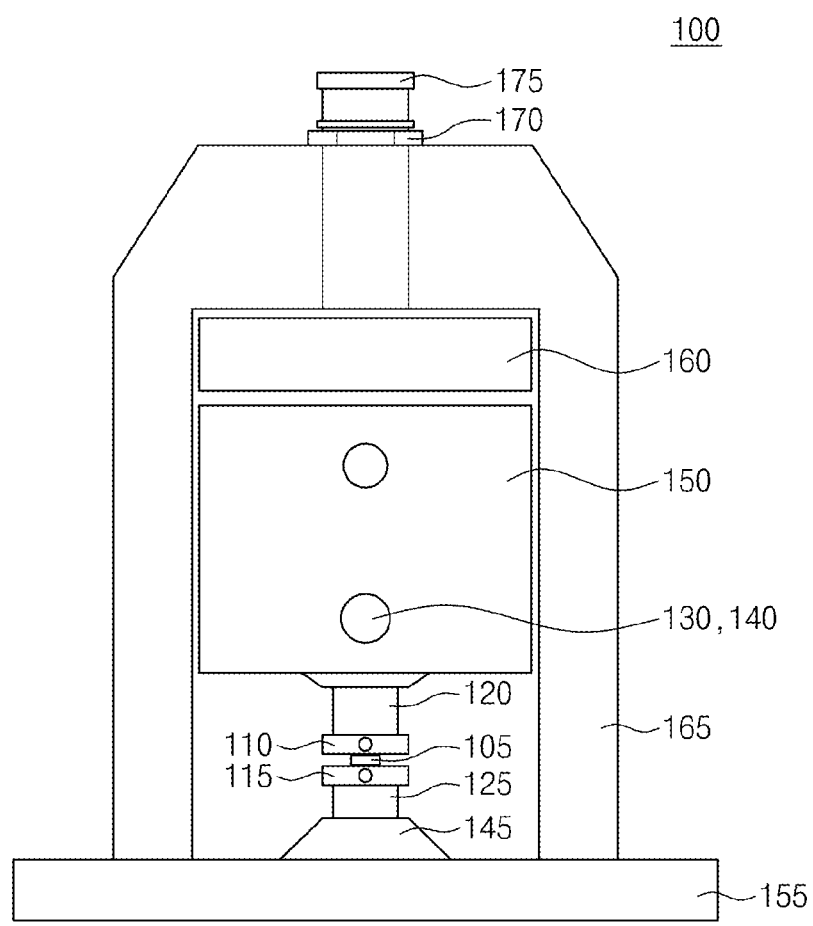
FIG. 7 is a top view illustrating the thermoelectric device measuring jig in an X direction in FIG. 6.

FIG. 7 is a top view illustrating the thermoelectric device measuring jig in an X direction in FIG. 6. Referring to FIG. 7, the first and second sensors 120 and 125, the high and low temperature plate electrodes 110 and 115, and the sample 105 may be located between the insulation unit 150 and the cooling chuck 145.

The cooling chuck 145 may be located in a center of the supporting plate 155. The insulation unit 150 may be located in the center supporting frame 165. The first and second sensors 120 and 125, the high and low temperature plate electrodes 110 and 115, and the sample 105 may be located between the insulation unit 150 and the cooling chuck 145. The first sensor 120 and the high temperature plate electrode 110 may be fixed being in contact with the insulation unit 150. The second sensor 125 and the low temperature plate electrode 115 may be fixed being in contact with the cooling chuck 145. The high temperature heater 140 and the fine control heater 130 may be installed in the insulation unit 150. The connecting cables of the high temperature heater 140 and the fine control heater 130 may be connected to the side of the insulation unit 150.

The fixing nut 170 of the air cylinder and the body 175 of the air cylinder may uniformly maintain pressure applied to the sample 105 and the high and low temperature plate electrodes 110 and 115. The pressure sensor 160 may measure the pressure applied to the sample 105. The pressure sensor 160 may uniformly maintain the pressure applied to the sample 105.

According to the embodiments, an apparatus and a method for effectively measuring properties of a thermoelectric device may be provided. Also, a thermocouple contact point of a thermoelectric plate electrode may be heated by an alternating current and simultaneously a change in temperature of the thermocouple contact point is tracked, thereby measuring properties of a sample of the thermoelectric device.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:
1. An apparatus for measuring a thermoelectric device comprising:

a high temperature heater controlling a temperature of a first side of a sample;

a low temperature heater controlling a temperature of a second side of the sample;

a fine control heater controlling the temperature of the first side of the sample by a smaller unit than the high temperature heater;

a temperature control and voltage measuring unit controlling the high temperature heater, the low temperature heater, and the fine control heater and measuring voltages of the first and second sides of the sample; and a thermal conductivity measuring unit measuring thermal conductivity of the sample by using a high temperature output voltage generated in the first side of the sample and a low temperature output voltage generated in the second side of the sample;

wherein the temperature control and voltage measuring unit comprises:

a first temperature controller applying a high temperature input voltage to the high temperature heater to control the temperature of the first side of the sample;

a first measurer applying a variation input voltage to control the temperature of the first side of the sample by a smaller unit than the high temperature heater and measuring the high temperature output voltage;

a second temperature controller applying a low temperature input voltage to the lower temperature heater to control the temperature of the second side of the sample; and a second measurer measuring the low temperature output voltage;

wherein the first measurer controls the fine control heater to vary by only a single unit of temperature and measures the high temperature output voltage according to the varying by the single unit of temperature.

2. The apparatus of claim 1, further comprising:

a high temperature plate electrode in contact with the first side of the sample; and a first sensor measuring a voltage and a current of the high temperature plate electrode to calculate the temperature of the first side of the sample, wherein the first temperature controller controls the high temperature input voltage according to the temperature of the first side of the sample, and wherein the first measurer measures the high temperature output voltage through the high temperature plate electrode and controls the variation input voltage according to the high temperature output voltage.

3. The apparatus of claim 1, further comprising:

a low temperature plate electrode in contact with the second side of the sample; and a second sensor measuring a voltage and a current of the low temperature plate electrode to calculate the temperature of the second side of the sample, wherein the second temperature controller controls the low temperature input voltage according to the temperature of the second side of the sample, and wherein the second measurer measures the low temperature output voltage through the low temperature plate electrode.

4. The apparatus of claim 3, wherein the temperature control and voltage measuring unit comprises a third measurer measuring a voltage and a current by a smaller unit than the second temperature controller, and wherein the third measurer calculates the temperature of the second side of the sample according to a voltage and a current of the low temperature plate electrode measured by the second sensor.

5. The apparatus of claim 1, wherein the first side of the sample is opposite to the second side of the sample.

6. An apparatus for measuring a thermoelectric device comprising:

a high temperature heater controlling a temperature of a first side of a sample;

a low temperature heater controlling a temperature of a second side of the sample;

a fine control heater controlling the temperature of the first side of the sample by a smaller unit than the high temperature heater;

a temperature control and voltage measuring unit controlling the high temperature heater, the low temperature heater, and the fine control heater and measuring voltages of the first and second sides of the sample; and a thermal conductivity measuring unit measuring thermal conductivity of the sample by using a high temperature output voltage generated in the first side of the sample and a low temperature output voltage generated in the second side of the sample;

wherein the thermal conductivity measuring unit comprises:

a frequency generator generating a reference voltage;

a thermoelectric voltage amplification part generating a lock-in voltage using the high and low temperature output voltages; and a lock-in amplifier measuring the thermal conductivity of the sample using the reference voltage and the lock-in voltage.

7. The apparatus of claim 6, wherein the thermoelectric voltage amplification part comprises:

a potentiometer connected to the sample in series and controlling resistance to remove a noise signal from the high and low temperature voltages; and a comparator comparing an output voltage of the potentiometer with the high and low temperature output voltages and outputting the lock-in voltage.

8. The apparatus of claim 7, wherein the thermoelectric voltage amplification part further comprises:

a first amplifier amplifying the output voltage of the potentiometer and transmitting the amplified output voltage to the comparator; and a second amplifier amplifying a voltage difference between the high and low temperature output voltages and transmitting the amplified voltage difference to the comparator.

9. The apparatus of claim 6, wherein the lock-in amplifier changes the lock-in voltage according to the reference voltage and outputs a thermoelectric voltage corresponding to a preset frequency.

10. A method of measuring a thermoelectric device, comprising:

using a high temperature heater to control a temperature of a first side of a sample;

using a low temperature heater to control a temperature of a second side of the sample;

using a fine control heater to control the temperature of the first side of the sample by a smaller unit than the high temperature heater;

using a temperature control and voltage measuring unit to control the high temperature heater, the low temperature heater, and the fine control heater and to measure voltages of the first and second sides of the sample; and using a thermal conductivity measuring unit to measure thermal conductivity of the sample by using a high temperature output voltage generated in the first side of the sample and a low temperature output voltage generated in the second side of the sample;

wherein using the temperature control and voltage measuring unit comprises:

using a first temperature controller to apply a high temperature input voltage to the high temperature heater to control the temperature of the first side of the sample;

using a first measurer to apply a variation input voltage to control the temperature of the first side of the sample by a smaller unit than the high temperature heater and to measure the high temperature output voltage;

using a second temperature controller to apply a low temperature input voltage to the lower temperature heater to control the temperature of the second side of the sample; and using a second measurer to measure the low temperature output voltage;

wherein the first measurer controls the fine control heater to vary by only a single unit of temperature and measures the high temperature output voltage according to the varying by the single unit of temperature.

* * * * *